US011080821B2

(12) United States Patent
Cooke et al.

(10) Patent No.: US 11,080,821 B2
(45) Date of Patent: Aug. 3, 2021

(54) AUTOMATED BENTHIC ECOLOGY SYSTEM AND METHOD FOR STEREOSCOPIC IMAGERY GENERATION

(71) Applicant: The United States of America as represented by the Secretary of the Navy, San Diego, CA (US)

(72) Inventors: Cheryl Ann Cooke, San Diego, CA (US); Steven Patrick Murphy, San Diego, CA (US); Kris Gibson, Sykesville, MD (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/367,679

(22) Filed: Mar. 28, 2019

(65) Prior Publication Data

US 2020/0311868 A1 Oct. 1, 2020

(51) Int. Cl.

| *G06T 3/40* | (2006.01) |
|---|---|
| *H04N 5/232* | (2006.01) |
| *H04N 13/204* | (2018.01) |
| *H04N 13/156* | (2018.01) |
| *G01N 33/18* | (2006.01) |
| *H04N 5/247* | (2006.01) |

(Continued)

(52) U.S. Cl.
CPC .......... *G06T 3/4038* (2013.01); *G01N 33/18* (2013.01); *H04N 5/23238* (2013.01); *H04N 5/247* (2013.01); *H04N 13/156* (2018.05); *H04N 13/204* (2018.05); *G06T 7/60* (2013.01); *H04N 2005/2255* (2013.01)

(58) Field of Classification Search
CPC ............ H04N 5/23238; H04N 19/597; H04N 13/243; H04N 13/117; H04N 21/816; H04N 13/239; H04N 13/344; H04N 13/111; H04N 13/161; H04N 5/247
See application file for complete search history.

(56) References Cited

U.S. PATENT DOCUMENTS

| 6,286,460 B1* | 9/2001 | Gudbjornsson ........ | A01K 61/90 |
|---|---|---|---|
| | | | 119/200 |
| 2004/0246333 A1* | 12/2004 | Steuart, III ............ | G03B 35/08 |
| | | | 348/36 |

(Continued)

*Primary Examiner* — Samira Monshi
(74) *Attorney, Agent, or Firm* — Naval Information Warfare Center, Pacific; Kyle Eppele; Susanna J. Torke

(57) ABSTRACT

A method for generating stereoscopic imagery comprising the steps of building an automated benthic ecology system comprising a high-resolution still camera, a high-resolution video camera, an environmental sensor package, a stereoscopic camera, and underwater housing, wherein the high-resolution video camera is configured for constant recording, turning the video camera on and hovering the ABES at the desired depth for a specific period of time acquiring imagery, wherein the imagery is automatically time-stamped with a date and time, extracting frames from the video, matching the timestamps on the photographs with the timestamps of the ROV log, which provides latitude, longitude and depth measurements, georeferencing each image using GeoSetter software, stitching imagery from the stereoscopic camera into a panoramic image using software.

2 Claims, 5 Drawing Sheets

(51) Int. Cl.
*H04N 5/225* (2006.01)
*G06T 7/60* (2017.01)

(56) References Cited

U.S. PATENT DOCUMENTS

| | | | | |
|---|---|---|---|---|
| 2015/0350552 | A1* | 12/2015 | Pryszo | H04N 5/23293 |
| | | | | 348/143 |
| 2016/0035096 | A1* | 2/2016 | Rudow | H04N 5/23293 |
| | | | | 348/135 |
| 2018/0322197 | A1* | 11/2018 | Hesterman | G06F 16/29 |
| 2019/0297363 | A1* | 9/2019 | Chirokov | H04N 21/21805 |
| 2020/0267947 | A1* | 8/2020 | Krossli | G01G 17/08 |

* cited by examiner

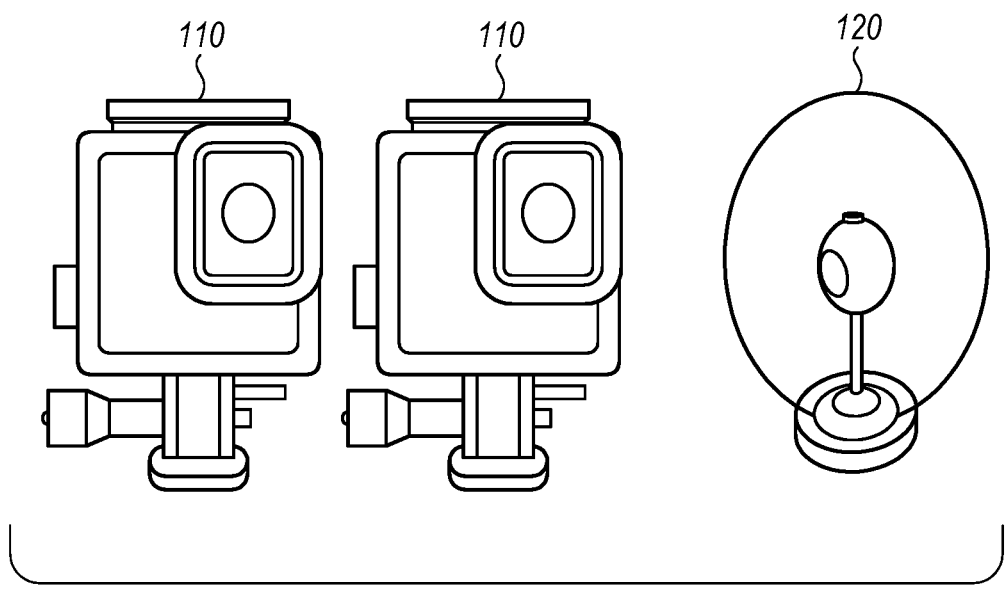
FIG. 1A
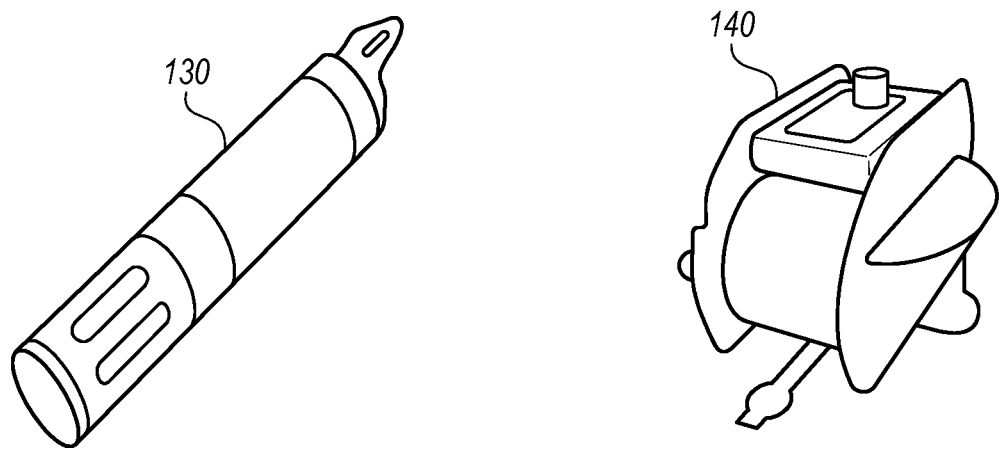
FIG. 1B  FIG. 1C

AUTOMATED BENTHIC ECOLOGY SYSTEM AND METHOD FOR STEREOSCOPIC IMAGERY GENERATION

FEDERALLY-SPONSORED RESEARCH AND DEVELOPMENT

Automated Benthic Ecology System and Method for Stereoscopic Imagery Generation is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil. Reference Navy Case Number 110622.

BACKGROUND

In the past, benthic habitats in areas of low visibility were either not surveyed at all or humans surveyed them on the rare occasion of clear quality conditions. Only small areas of vertical structures were assessed and species' abundance was grossly overestimated to the size of the entire structure, thus causing issues with environmental compliance and permitting actions. Only certified and specially-trained divers can dive in areas where unexploded ordnance (UXO) is present, which is extremely costly and time-consuming.

The Automated Benthic Ecology System (ABES) is a small, portable remotely operated vehicle (ROV) used to conduct photomosaicing surveys of: (1) biological communities inhabiting vertical structures such as piers and quay walls, (2) biological communities in areas of known UXO and buried munitions, (3) pier and quay wall integrity to investigate for cracks, leaks and other structural issues, and (4) compromised integrity of a ship's hull for planning purposes of the salvage operation as well as pre- and post-salvage surveys of biological impacts. The ABES obtains high-resolution imagery of the site, along with water quality information to provide a more complete ecological understanding of areas of interest that are inaccessible and/or areas that pose human health or safety access issues. Adding a stereoscopic payload and three-dimensional model generation capability has made the ABES capable of collapsing four surveys into one survey and providing a holistic view of the area of interest.

BRIEF DESCRIPTION OF THE DRAWINGS

FIGS. 1A-1C show the three components that, when combined, comprise an Automated Benthic Ecology System (ABES).

DETAILED DESCRIPTION OF SOME EMBODIMENTS

Reference in the specification to "one embodiment" or to "an embodiment" means that a particular element, feature, structure, or characteristic described in connection with the embodiments is included in at least one embodiment. The appearances of the phrases "in one embodiment", "in some embodiments", and "in other embodiments" in various places in the specification are not necessarily all referring to the same embodiment or the same set of embodiments.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

Additionally, use of the "a" or "an" are employed to describe elements and components of the embodiments herein. This is done merely for convenience and to give a general sense of the invention. This detailed description should be read to include one or at least one and the singular also includes the plural unless it is obviously meant otherwise.

FIGS. 1A-1C show the three necessary components that, when combined, comprise one Automated Benthic Ecology System (ABES): FIG. 1A shows photomosaicing technology 110 and stereoscopic camera 120. Stereoscopic camera 120 comprises a 360-degree camera with an underwater bubble housing. FIG. 1B shows an environmental sensor package 130. Environmental sensor package 130 is a multi-parameter sonde used for monitoring water quality in both fresh and salt water. It is equipped with pH, temperature, depth, conductivity (salinity), turbidity, blue-green algae, and ambient light sensors. FIG. 1C shows a tethered underwater remotely operated vehicle (ROV) 140.

Figure 2:
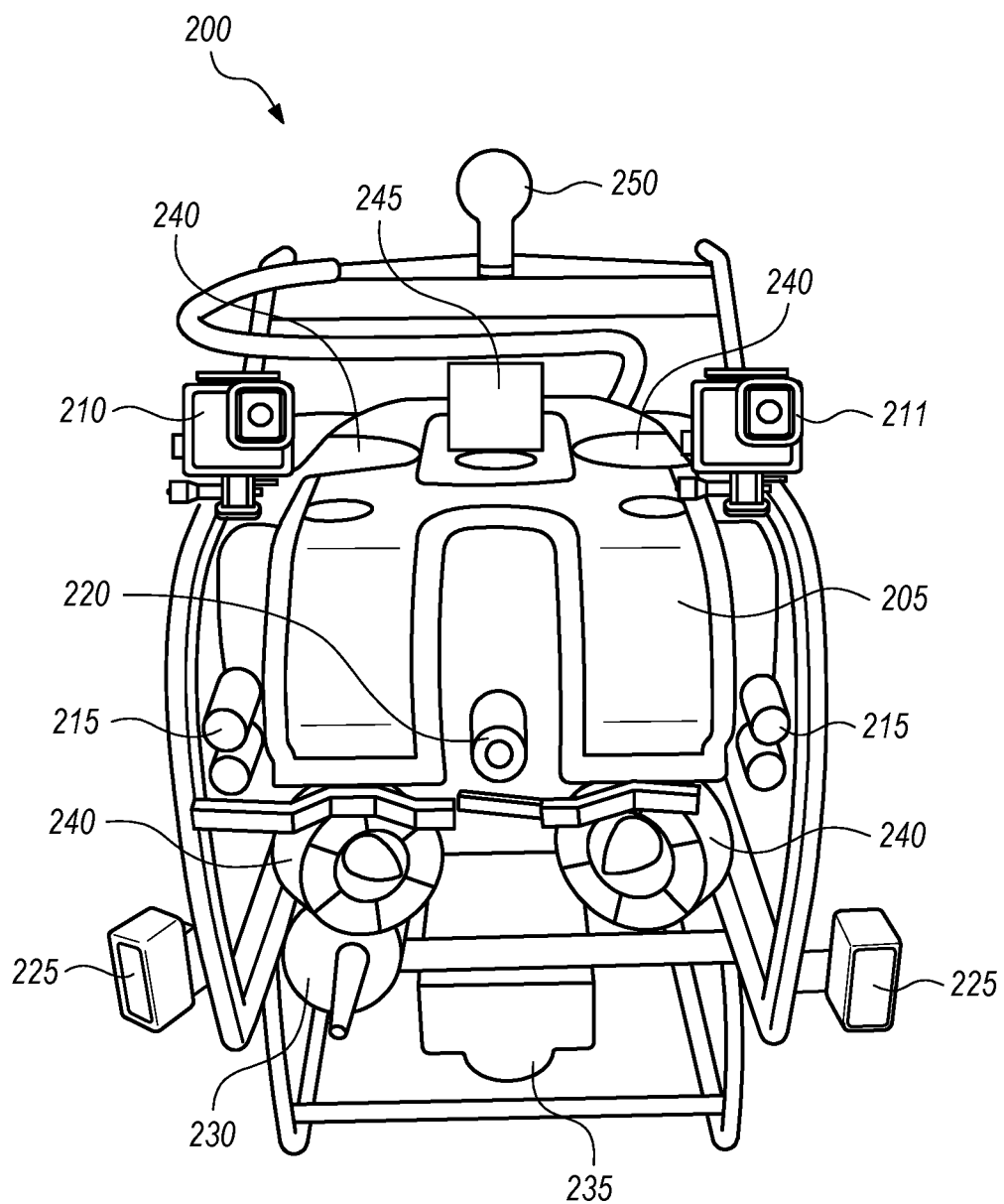
FIG. 2 shows a front view of one embodiment of an Automated Benthic Ecology System (ABES).

FIG. 2 shows a front view of one embodiment of an ABES 200. ABES 200 is anchored with a remotely operated vehicle (ROV) 205. ROV 205 comprises a photomosaicing system including a high-resolution still camera 210 and a high-resolution video camera 211. High-resolution still camera 210 is programmed to take 30 frames per second and the interval timer function is set to once every 0.5 seconds. High-resolution video camera 211 is set for constant recording. ROV 205 can also electrically connect via a tether (FIG. 3) to a computer for running mission planning, real-time monitoring of ABES 200, and post-mission analysis and replay (control electronics). A shippable rack for these control electronics and data storage are present on the shore or boat from which ABES is deployed.

One embodiment of ROV 205 is the Sensor-Based Stabilized Remotely Operated vehicle Waterbourne IED Identification and Neutralization (SSR-WIN). Underwater ROV 205 is off-loaded from a boat and into the water column, in some instances by davit, or small crane. It can come with the capability to interrupt and resume a mission from where it left off. ROV 205 also has graphical user interfaces that allow for 3-D modeling, mosaic mapping and coverage maps. ROV 205 has a Tiny Optical Gyro System (TOGS) (located underneath ROV 205 and not shown here) that acts as a true north seeking fiber optic gyro. TOGS is an internal navigational compass—it talks to the software the controls ROV 205. The TOGS provides pitch, roll, and heave outputs to accurately track all aspects of ROV 205's motion. ROV 205 has software that can be programmed to auto-correct itself when it veers off the course that has been planned into it. If ROV 205 cannot auto-correct itself (for example, if it loses GPS signal), the Status window of ROV 205 GUI provides feedback about the health status of the system. Elements of the system that are healthy are shown in green; elements that are showing a fault are highlighted in orange or red. Clicking on the alarm displays the root cause and suggested response to be fixed immediately in the field.

Turning back to FIG. 2, ROV 205 has a plurality of lights 215. ROV 205 has a camera 220, multiple external strobes 225 and an environmental sensor package 230. Environmental sensor package 230 is programmed to take measurements of temperature, pH, salinity, turbidity, chlorophyll, blue-green algae and photosynthetically active radiation of the water ROV 205 is swimming in every minute. Environmental sensor package 230 is used for monitoring water quality in both fresh and saltwater. Environmental sensor package 230 should be optimized for long-term, unattended deployments. It should also have a central cleaning system that wipes away fouling. Environmental sensor package 230 can include temperature, conductivity, turbidity, salinity, ambient light and blue-green algae sensors. One embodiment of environmental sensor 230 can be the OTT Hydromet Hydrolab DS5x, which is a multi-parameter sonde. This particular embodiment includes a brush design that has robust fibers that will not separate over time and it has a single motor to clean the entire suite of sensors. ROV 205 has a Doppler Velocity Log (DVL) 235 that uses a phased-array transducer to monitor motion and speed of ROV 205. DVL 235 provides a bottom track mode that augments ROV 205's ability to conduct navigation and track-keeping. DVL 235 provides a feed to the TOGS to dampen out the integration errors by providing a measured speed over ground. This way ROV 205 can report its position in WGS84 latitude and longitude. Multiple thrusters 240 power the movement of ROV 205. ROV 205 has a GPS 245, and after it is fully warmed up with current Almanac and Ephemeris data system, GPS 245 establishes the geographic latitude and longitude of ROV 205. This latitude and longitude is passed to the TOGS which takes the starting point of ROV 205 when it submerges and integrates it over time to track the position of ROV 205 underwater. Every time GPS 245 reaches the surface of the water it re-locates itself based on its new GPS reading. ROV 205 also has a light sensor 250.

Figure 3:
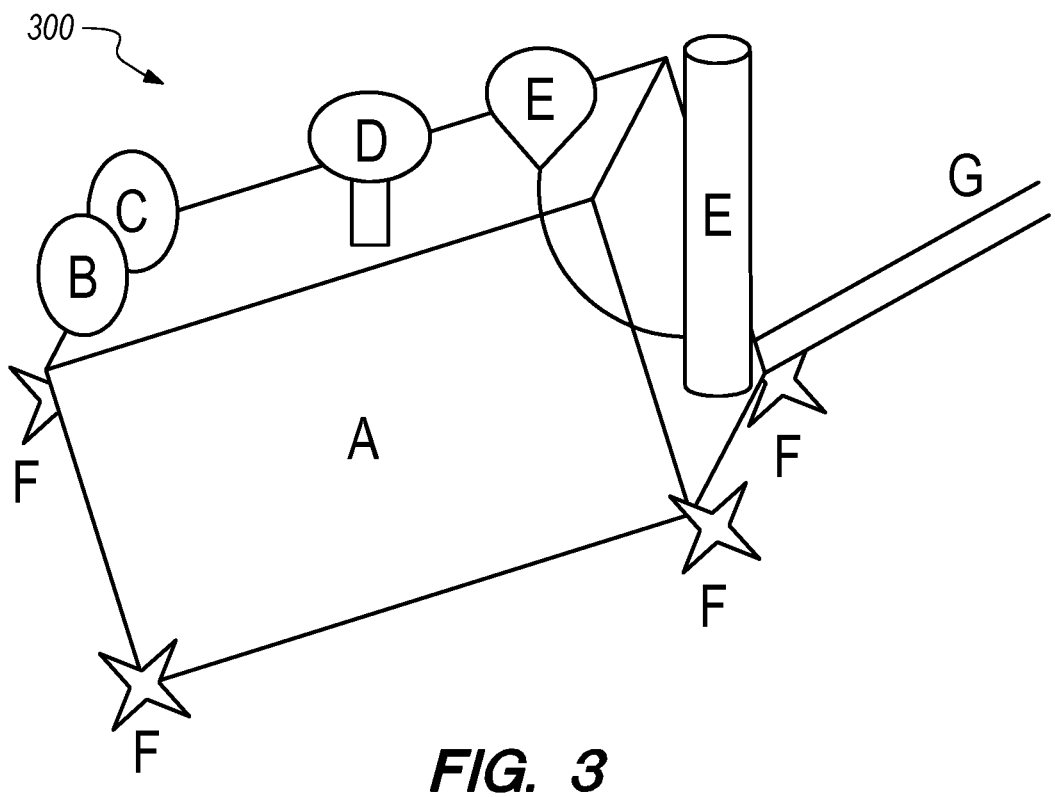
FIG. 3 shows a front view of an alternate embodiment of an ABES.

FIG. 3 shows a front view of an Automated Benthic Ecology System (ABES) 300. ABES 300 is anchored by an underwater remotely operated vehicle (ROV) (A). ROV (A) has a highly accurate location tracking capability and the capability to operate semi-autonomously. ABES 300 also has a high-resolution still camera (B) with a video camera set-up (C). ABES 300 has a stereoscopic camera (D) and an ambient saltwater sensor package (E). ABES 300 has a tether (G) that connects ROV (A) to a laptop. Tether (G) is the communications link that tells the ROV how to act. ABES 300 has a plurality of thrusters (F) that generate a propulsive force to move ROV (A) either vertically or horizontally or maintains position.

Figure 4:
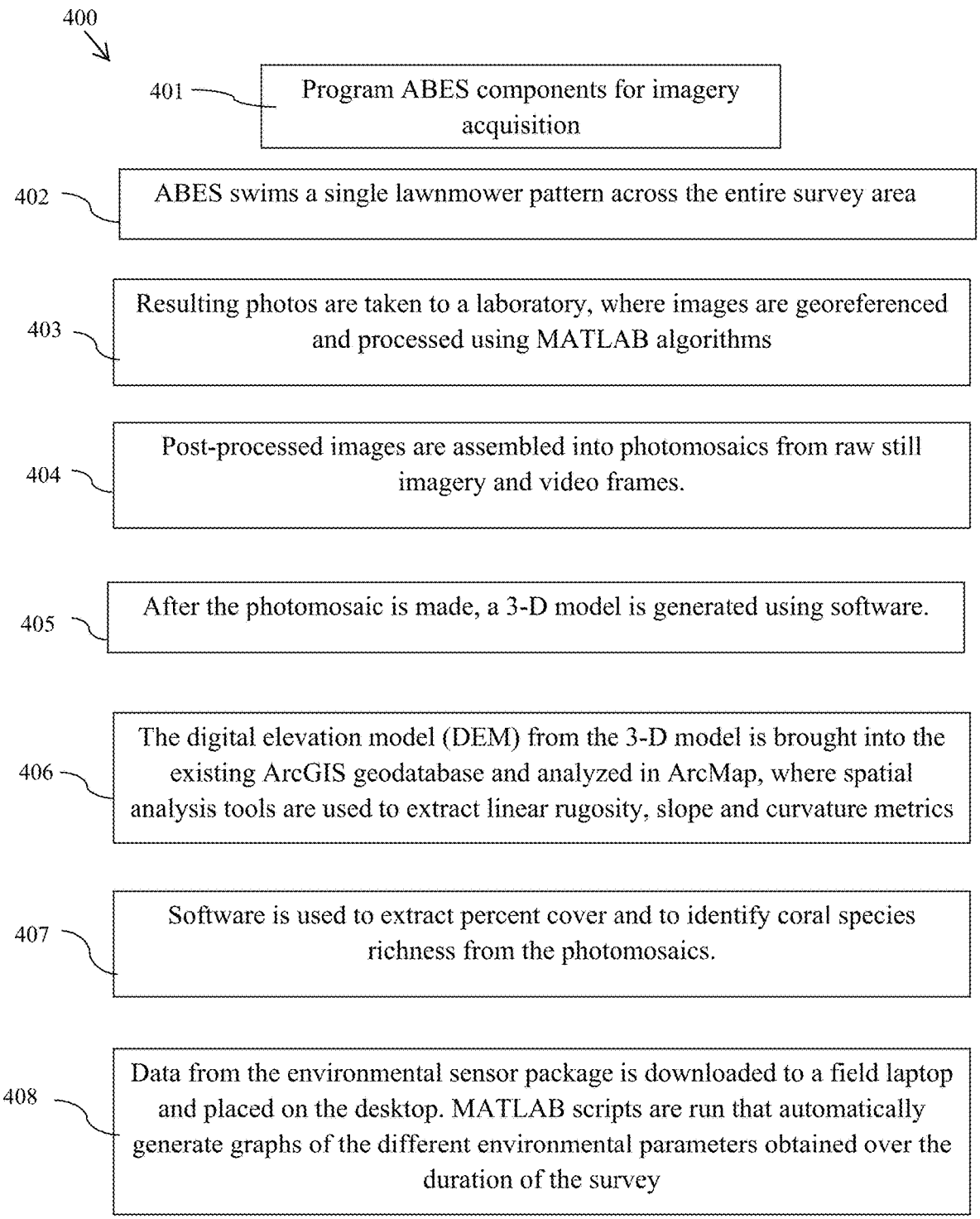
FIG. 4 shows a flow-chart demonstrating the photomosaic and 3-D model generation process.

FIG. 4 shows a flow-chart demonstrating a photomosaic and 3-D model generation process 400. In a first step 401, an ABES comprising a high-resolution still camera, a high-resolution video camera, and an environmental sensor package is programmed such that the high-resolution still camera takes 30 frames per second and the interval timer function is set to once every 0.5 seconds. The high-resolution video camera is set for constant recording. The environmental sensors are programmed to take measurements of temperature, pH, salinity, turbidity, chlorophyll, blue-green algae and photosynthetically active radiation of the water the ABES is swimming in every minute. In the next step 402, ABES swims a single lawnmower pattern across the entire survey area with the cameras facing the survey area of interest while staying approximately one meter in front of the area of interest so as not to disturb any organisms growing on it. Each still photograph is time-stamped with a date and time. Step 403 takes place in a laboratory, where the timestamps on the photographs are matched with the timestamps of the ROV log, which provides latitude, longitude and depth measurements. Each image is georeferenced using GeoSetter software and the georeferenced images are then post-processed using the enhanced MATLAB algorithms for de-blurring, light and color enhancement.

In step 404, these post-processed images are then brought into a MATLAB photomosaicing applications to assemble photomosaics from the raw still imagery and video frames. In step 405, after the photomosaic have been created, software is used to extract percent cover and other metrics by a marine ecologist. In one embodiment, Coral Point Count with Excel extensions (CPCe) software is used. CPCe is the primary program used to extract benthic cover and to identify coral species richness from the photomosaics. The photomosaic viewer, however, is used to "zoom in" on the still images acquired during the survey to aid identification if necessary. The photomosaic tiffs and associated Excel data will also be brought into the existing ArcGIS geospatial database for future use.

In step 406, a 3-D model is generated using the AgiSoft PhotoScan software. The digital elevation model (DEM) from the 3-D model is brought into the existing ArcGIS geodatabase and analyzed in ArcMap, where spatial analysis tools are used to extract linear rugosity, slope and curvature metrics.

For step 407, also back in the lab, data from the environmental sensor package is downloaded to a field laptop and placed on the desktop. MATLAB scripts are run that automatically generate graphs of the different environmental parameters obtained over the duration of the survey.

Figure 5:
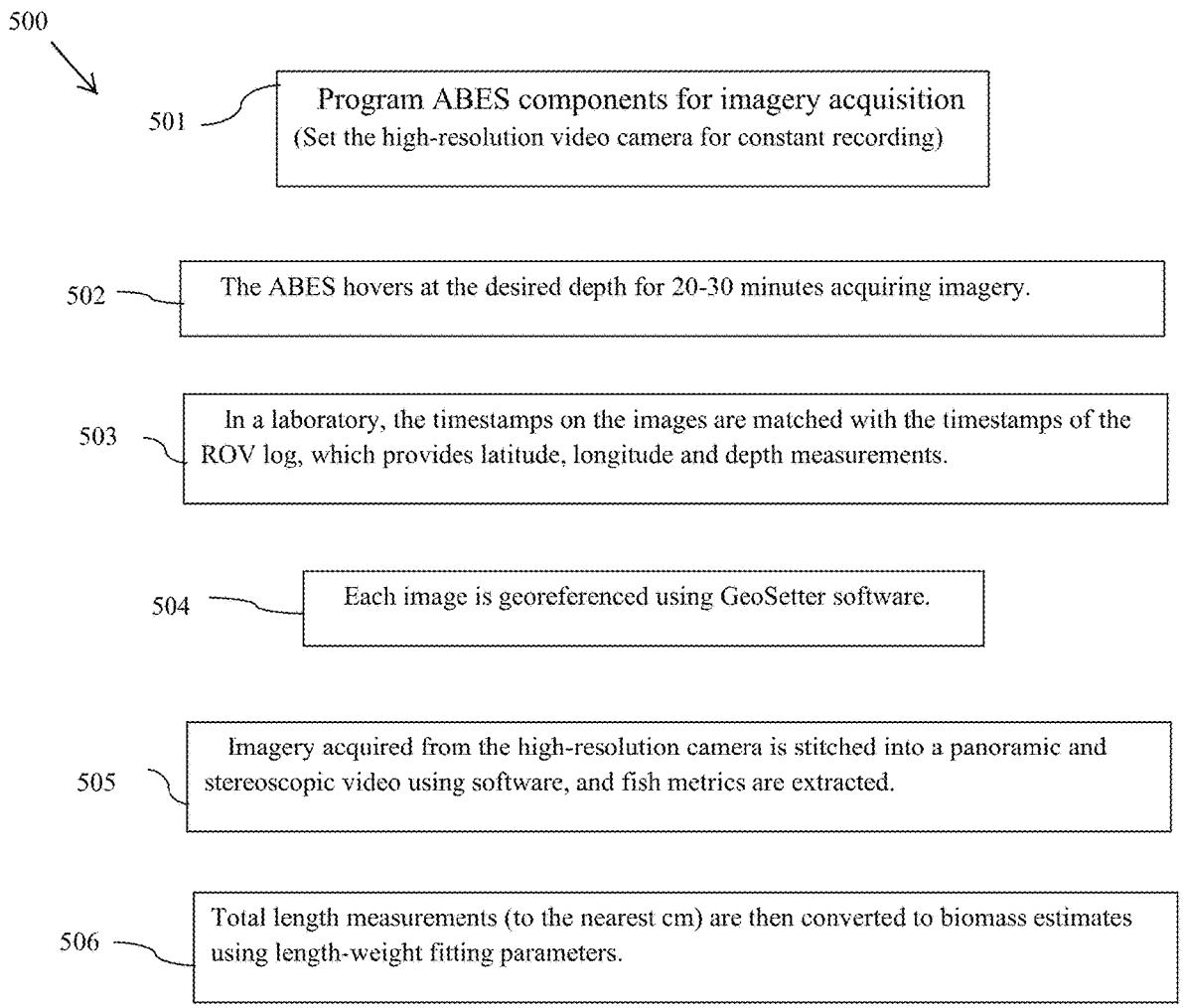
FIG. 5 shows a flow-chart demonstrating the stereoscopic imagery generation process.

FIG. 5 shows a flow-chart demonstrating the stereoscopic imagery generation process 500 for fish metrics. In first step 501, an ABES comprises a high-resolution still camera, a high-resolution video camera, an environmental sensor package, a stereoscopic camera and underwater housing, and the high-resolution video camera is set for constant recording. In step 502, the video camera is turned on and the ABES hovers at the desired depth for 20-30 minutes acquiring imagery. Each frame extracted from the video is automatically time-stamped with a date and time. In step 503, in a laboratory the timestamps on the photographs are matched with the timestamps of the ROV log, which provides latitude, longitude and depth measurements. In step 504, each image is georeferenced using GeoSetter software.

In step 505, imagery acquired from the stereoscopic camera is stitched into a panoramic image using software, and fish metrics are extracted. One embodiment uses the Samsung Gear 360 Action Director software for stitching imagery, and another embodiment uses the Image J, CPCE or SEBASTES software for extracting fish metrics.

For step 506, total length measurements (to the nearest cm) are then converted to biomass estimates using length-weight fitting parameters. To estimate the fish biomass from underwater length observations, fitting parameters are obtained from NOAA's Southeast Fisheries Science Center and FishBase. Visual length estimates will be converted to weight using the formula M=(a)*(Lb), where M=mass in grams, L=standard length in mm and "a" and "b" are fitting parameters. The trophic categories included are piscivores, herbivores, detritivores, mobile and sessile invertebrate feeds and zooplanktivores.

Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method for generating stereoscopic imagery comprising the steps of:
    building an automated benthic ecology system comprising a high-resolution still camera, a high-resolution video camera, an environmental sensor package, a stereoscopic camera, and underwater housing, wherein the high-resolution video camera is configured for constant recording;
    turning the high-resolution video camera on and hovering the automated benthic ecology system at a desired depth for a specific period of time acquiring imagery, wherein the imagery is automatically time-stamped with a date and time;
    extracting frames from the high-resolution video camera;
    matching the timestamps on the imagery with the timestamps of a remotely operated vehicle log, which provides latitude, longitude and depth measurements;
    georeferencing each image using GeoSetter software;
    stitching imagery from the stereoscopic camera into a panoramic image using software;
    using the panoramic image to extract fish metrics comprising total length measurements;
    converting the total length measurements to biomass estimates using length-weight fitting parameters.

2. The method of claim 1, further comprising the step of converting visual length estimates to mass using standard species-specific fitting parameters and total length measurements derived from the stereoscopic imagery.

* * * * *